United States Patent [19]
Tanzer et al.

[11] Patent Number: 5,562,645
[45] Date of Patent: Oct. 8, 1996

[54] ARTICLE WITH SOFT ABSORBENT PULP SHEET

[75] Inventors: Richard W. Tanzer, Neenah; Mark L. Robinson; Fung-Jou Chen, both of Appleton; Richard J. Kamps, Wrightstown; Lorry F. Sallee, Pine River, all of Wis.

[73] Assignee: Kimberly-Clark Corporation, Neenah, Wis.

[21] Appl. No.: 455,778

[22] Filed: May 31, 1995

[51] Int. Cl.$^6$ .............................. A61F 13/15; A61F 13/20
[52] U.S. Cl. ......................... 604/367; 604/358; 604/365; 604/368; 604/372; 604/378
[58] Field of Search ............................ 604/358, 365–368, 604/372, 378, 385.1

[56] References Cited

U.S. PATENT DOCUMENTS

| | | |
|---|---|---|
| 3,478,142 | 11/1969 | Greene . |
| 3,612,055 | 10/1971 | Mesek et al. ........................ 604/378 |
| 3,763,863 | 10/1973 | Mesek et al. ........................ 604/378 |
| 3,779,246 | 12/1973 | Mesek et al. ........................ 604/378 |
| 3,901,236 | 8/1975 | Assarsson et al. . |
| 4,055,180 | 10/1977 | Karami .............................. 604/368 |
| 4,076,663 | 2/1978 | Masuda et al. . |
| 4,286,082 | 8/1981 | Tsubakimoto et al. . |
| 4,376,147 | 3/1983 | Byrne et al. . |
| 4,381,783 | 5/1983 | Elias ............................... 604/368 |
| 4,551,142 | 11/1985 | Kopolow ........................... 604/368 |
| 4,663,220 | 5/1987 | Wisneski et al. . |
| 4,806,300 | 2/1989 | Walton et al. . |
| 4,942,005 | 7/1990 | Pollock et al. . |
| 5,028,224 | 7/1991 | Pieper et al. . |
| 5,141,685 | 8/1992 | Maier et al. . |
| 5,143,774 | 9/1992 | Cancio et al. . |
| 5,226,992 | 7/1993 | Morman . |
| 5,242,435 | 9/1993 | Murji et al. . |
| 5,387,385 | 2/1995 | Murji et al. . |
| 5,411,497 | 5/1995 | Tanzer et al. ....................... 604/378 |
| 5,425,725 | 6/1995 | Tanzer et al. ....................... 604/378 |
| 5,429,629 | 7/1995 | Latimer et al. ...................... 604/384 |
| 5,433,715 | 7/1995 | Tanzer et al. ....................... 604/378 |
| 5,460,622 | 10/1995 | Dragoo et al. ...................... 604/378 |

FOREIGN PATENT DOCUMENTS

| | | |
|---|---|---|
| 0217032A3 | 4/1987 | European Pat. Off. . |
| 0339461B1 | 11/1989 | European Pat. Off. . |
| 0523744A1 | 1/1993 | European Pat. Off. . |
| 2254255 | 10/1992 | United Kingdom . |
| WO87/01678 | 3/1987 | WIPO . |
| WO94/10953 | 5/1994 | WIPO . |
| WO94/10954 | 5/1994 | WIPO . |

*Primary Examiner*—John G. Weiss
*Assistant Examiner*—P. Zuttarelli
*Attorney, Agent, or Firm*—Paul Yee

[57] ABSTRACT

The present invention provides a distinctive article which includes at least one absorbent, fibrous web layer which is substantially non-hydroentangled. The fibrous web layer can have a basis weight of at least about 60 gsm, and a density of not more than about 0.25 gm/cc. The fibrous web layer can further have a peak geometric mean tensile strength of at least about 250 grams-force per centimeter of width, and can have a fiber content in which at least about 90 wt % of the fibers are composed of fibers having a fiber length of not more than about 0.4 inch (about 1 cm). In particular configurations, the article includes a backsheet layer, and a liquid permeable topsheet layer which is disposed in facing relation with the backsheet layer. An absorbent structure is interposed between the backsheet layer and the topsheet layer, and the absorbent structure has an overall absorbent capacity of at least about 300 grams of saline.

22 Claims, 13 Drawing Sheets

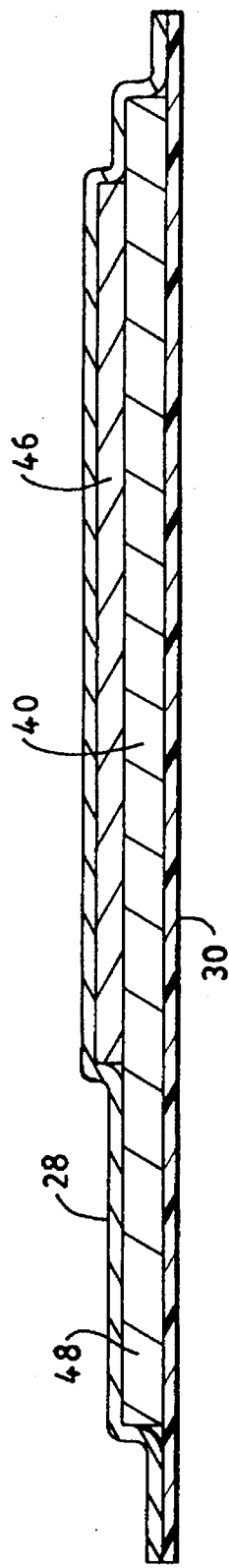
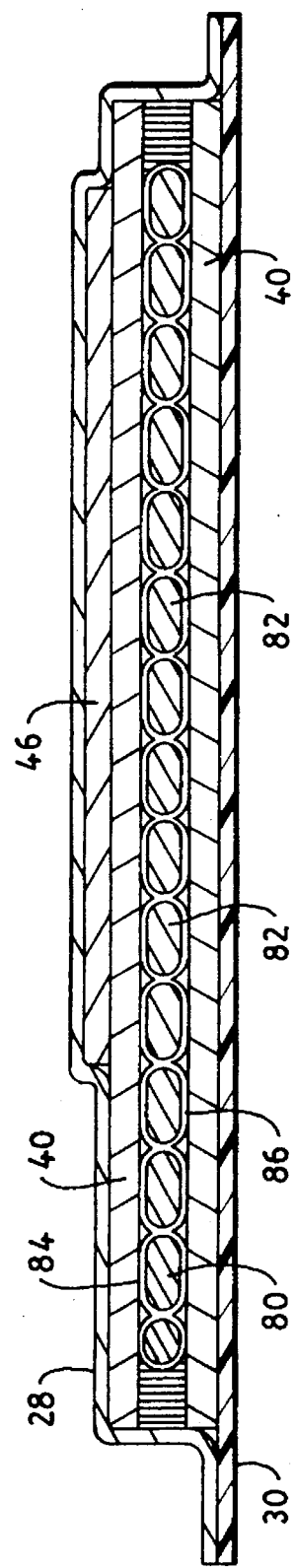

| MATERIAL DESCRIPTIONS | | Basis Wt. Per Sheet (gsm) | Density (g/cc) | Peak Geo. MeanTensile Str.(g force /cm) | COMPOSITION | | FIBER LENGTH | |
|---|---|---|---|---|---|---|---|---|
| No. | Material | | | | % Cellulose | % Binder | Wt.% Fibers >1cm | Wt.% Fibers >3cm |
| 1 | Bleached Kraft wood pulp, fiberized | 222 | 0.11 | 23 | 100% | 0% | 0% | 0% |
| 2 | Creped tissue paper | 17 | 0.10 | 109 | 100% | 0% | 0% | 0% |
| 3 | BOUNTY® towel | 42 | 0.07 | 326 | 98% | 2% | 0% | 0% |
| 4 | HI DRI® towel | 34 | 0.04 | 226 | 99% | 1% | 0% | 0% |
| 5 | JOB SQUAD® towel | 85 | 0.09 | 191 | 97% | 3% | 0% | 0% |
| 6 | WORK HORSE® manufactured rags | 89 | 0.17 | 721 | 85% | 15% | 15% | 15% |
| 7 | HUGGIES® Baby Wipes basesheet(dry) | 75 | 0.07 | 201 | 65% | 35% | 20% | 10% |
| 8 | DEPEND® Undergarment absorbent core | 442 | 0.09 | 12 | 92% | 2% | 2% | 2% |
| 9 | HUGGIES® diaper absorbent core | 704 | 0.20 | 24 | 60% | 0% | 0% | 0% |
| 10 | Wet-pressed pulpboard basesheet | 275 | 0.45 | 4,109 | 100% | 0% | 0% | 0% |
| 11 | Wet-pressed pulpboard basesheet | 168 | 0.40 | 2,449 | 100% | 0% | 0% | 0% |
| 12 | Wet-pressed pulpboard microstrained sheet | 166 | 0.30 | 500 | 100% | 0% | 0% | 0% |
| 13 | Wet-pressed pulpboard basesheet | 260 | 0.30 | 2,266 | 100% | 0% | 0% | 0% |

FIG. 9A

| MATERIAL DESCRIPTIONS | | | | Peak Geo. MeanTensile Str.(g force /cm) | COMPOSITION | | FIBER LENGTH | |
|---|---|---|---|---|---|---|---|---|
| No. | MATERIAL | Basis Wt.Per Sheet (gsm) | DENSITY (g/cc) | | % Cellulose | % Binder | Wt.% Fibers >1cm | Wt.% Fibers >3cm |
| 14 | Through-air dried pulpboard basesheet | 467 | 0.14 | 2,329 | 100% | 0% | 0% | 0% |
| 15 | Wet-pressed pulpboard basesheet | 163 | 0.27 | 1,247 | 100% | 0% | 0% | 0% |
| 16 | Wet-pressed pulpboard microstrained sheet | 151 | 0.25 | 341 | 100% | 0% | 0% | 0% |
| 17 | Through-air dried pulpboard basesheet | 167 | 0.12 | 1,069 | 100% | 0% | 0% | 0% |
| 18 | Through-air dried pulpboard basesheet | 337 | 0.14 | 2,036 | 100% | 0% | 0% | 0% |
| 19 | Wet-pressed pulpboard microstrained sheet | 255 | 0.25 | 493 | 100% | 0% | 0% | 0% |
| 20 | Through-air dried pulpboard microstrained sheet | 326 | 0.18 | 539 | 100% | 0% | 0% | 0% |
| 21 | Through-air dried pulpboard microstrained sheet | 282 | 0.23 | 941 | 100% | 0% | 0% | 0% |
| 22 | Through-air dried pulpboard microstrained sheet | 178 | 0.22 | 310 | 100% | 0% | 0% | 0% |
| 23 | Through-air dried pulpboard microstrained sheet | 441 | 0.18 | 1,023 | 100% | 0% | 0% | 0% |

FIG. 9B

| | | MATERIAL DESCRIPTIONS | | | | PROPERTIES | | | | | ABSORBENCY | |
|---|---|---|---|---|---|---|---|---|---|---|---|---|
| Sample ID No. | Base Sheet ID | Material | Softwood Fiber Content | | Basis Wt/Sht (gsm) | Density (g/cc) | Peak Geom. Mean Tensile Strnth. (g force/ cm width) | Stiff-ness (SGU) | Thck-ness (mm) | Stiffness ÷ Thickness (SGU/mm) | 45° Liquid Intake (g/g) | Blotter Test — Liquid Expressed (g/g) |
| | | | Untrtd | Cross linked | | | | | | | | |
| 10 | A-1 | Wet-pressed pulpboard basesheet | 100% | 0% | 275 | 0.45 | 4,109 | — | — | — | 2.4 | — |
| 11 | B-1 | Wet-pressed pulpboard basesheet | 100% | 0% | 168 | 0.40 | 2,449 | 1,780 | 0 | 4,272 | 2.6 | 2.4 |
| 12 | B-2 | Wet-pressed pulpboard microstrained sheet | 100% | 0% | 166 | 0.30 | 500 | 144 | 1 | 263 | 4.0 | 3.8 |
| 13 | C-1 | Wet-pressed pulpboard basesheet | 60% | 40% | 260 | 0.30 | 2,266 | 4,174 | 1 | 4,854 | 3.5 | 3.3 |
| 14 | H-1 | Through-air dried pulpboard basesheet | 60% | 40% | 467 | 0.14 | 2,329 | 15,804 | 3 | 4,685 | 6.6 | 6.5 |
| 15 | D-1 | Wet-pressed pulpboard basesheet | 60% | 40% | 163 | 0.27 | 1,247 | 1,608 | 1 | 2,711 | 3.5 | 3.3 |
| 16 | D-2 | Wet-pressed pulpboard microstrained sheet | 60% | 40% | 151 | 0.25 | 341 | 112 | 1 | 186 | 5.1 | 5.3 |
| 17 | E-1 | Through-air dried pulpboard basesheet | 60% | 40% | 167 | 0.12 | 1,069 | 2,128 | 1 | 1,471 | 7.3 | 7.5 |
| 18 | F-1 | Through-air dried pulpboard basesheet | 60% | 40% | 337 | 0.14 | 2,036 | 8,857 | 2 | 3,685 | 6.7 | 6.7 |

FIG. 10A

| MATERIAL DESCRIPTIONS | | | | PROPERTIES | | | | | | ABSORBENCY | |
|---|---|---|---|---|---|---|---|---|---|---|---|
| Sample ID No. | Base Sheet ID | Material | Softwood Fiber Content | | Basis Wt/Sht (gsm) | Density (g/cc) | Peak Geom. Mean Tensile Strnth. (g force/ cm width) | Stiff- ness (SGU) | Thck- ness (mm) | Stiffness÷ Thickness (SGU/mm) | 45° Liquid Intake (g/g) | Blotter Test — Liquid Expressed (g/g) |
| | | | Untrtd | Cross linked | | | | | | | | |
| 19 | C-2 | Wet-pressed pulpboard microstrained sheet | 60% | 40% | 255 | 0.25 | 493 | 261 | 1 | 259 | 4.9 | 5.0 |
| 20 | F-2 | Through-air dried pulpboard microstrained sheet | 60% | 40% | 326 | 0.18 | 539 | 539 | 2 | 301 | 6.5 | 6.7 |
| 21 | G-2 | Through-air dried pulpboard microstrained sheet | 100% | 0% | 282 | 0.23 | 941 | 554 | 1 | 443 | 4.9 | 4.7 |
| 22 | E-2 | Through-air dried pulpboard microstrained sheet | 60% | 40% | 178 | 0.22 | 310 | 200 | 1 | 243 | 7.4 | 7.7 |
| 23 | H-2 | Through-air dried pulpboard microstrained sheet | 60% | 40% | 441 | 0.18 | 1,023 | 1,653 | 2 | 689 | 6.1 | 6.2 |

FIG. 10B

TENSILE STRENGTH

| Sample ID No. | Number Of Values | | PEAK GEOMETRIC MEAN TENSILE STRENGTH (g force/cm width) GMTS | | | log (GMTS) | | |
|---|---|---|---|---|---|---|---|---|
| | m.d. | c.d. | MIN. | AVG. | MAX. | MIN. | AVG. | MAX. |
| 1 | 4 | 5 | 18 | 23 | 26 | 1.25 | 1.36 | 1.41 |
| 2 | 3 | 3 | 102 | 109 | 113 | 2.01 | 2.04 | 2.05 |
| 3 | 3 | 3 | 308 | 326 | 355 | 2.49 | 2.51 | 2.55 |
| 4 | 3 | 3 | 205 | 226 | 242 | 2.31 | 2.35 | 2.38 |
| 5 | 3 | 3 | 184 | 191 | 202 | 2.26 | 2.28 | 2.31 |
| 6 | 3 | 3 | 640 | 721 | 830 | 2.81 | 2.86 | 2.92 |
| 7 | 3 | 3 | 184 | 201 | 220 | 2.26 | 2.30 | 2.34 |
| 8 | 3 | 3 | 7 | 12 | 20 | 0.84 | 1.08 | 1.29 |
| 9 | 3 | 3 | 18 | 24 | 31 | 1.25 | 1.37 | 1.49 |
| 10 | 3 | 3 | 3,814 | 4,109 | 4,347 | 3.58 | 3.61 | 3.64 |
| 11 | 4 | 4 | 2,325 | 2,449 | 2,672 | 3.37 | 3.39 | 3.43 |
| 12 | 4 | 4 | 465 | 500 | 541 | 2.67 | 2.70 | 2.73 |
| 13 | 3 | 3 | 2,169 | 2,266 | 2,401 | 3.34 | 3.35 | 3.38 |
| 14 | 3 | 3 | 2,103 | 2,329 | 2,656 | 3.32 | 3.37 | 3.42 |
| 15 | 3 | 3 | 1,160 | 1,247 | 1,308 | 3.06 | 3.10 | 3.12 |
| 16 | 3 | 3 | 326 | 341 | 355 | 2.51 | 2.53 | 2.55 |
| 17 | 3 | 3 | 1,029 | 1,069 | 1,116 | 3.01 | 3.03 | 3.05 |
| 18 | 3 | 3 | 1,973 | 2,036 | 2,099 | 3.30 | 3.31 | 3.32 |
| 19 | 3 | 3 | 445 | 493 | 552 | 2.65 | 2.69 | 2.74 |
| 20 | 3 | 3 | 510 | 539 | 571 | 2.71 | 2.73 | 2.76 |
| 21 | 3 | 3 | 895 | 941 | 995 | 2.95 | 2.97 | 3.00 |
| 22 | 4 | 3 | 300 | 310 | 319 | 2.48 | 2.49 | 2.50 |
| 23 | 3 | 3 | 932 | 1,023 | 1,080 | 2.97 | 3.01 | 3.03 |

FIG. 11

ARTICLE WITH SOFT ABSORBENT PULP SHEET

FIELD OF THE INVENTION

The present invention relates to articles, particularly structures which are useful in absorbent products. More particularly, the invention relates to absorbent articles which include an absorbent structure composed of one or more layers of a distinctive fibrous web.

BACKGROUND OF THE INVENTION

Absorbent articles, such as disposable diapers, have included absorbent structures composed of conventional materials, such as creped wading, cellulosic wood pulp fluff, fibrous coform materials, superabsorbent particles, tissues and combinations thereof. For example, conventional absorbent structures have been composed of mixtures of superabsorbent polymer material and wood pulp fluff, and mixtures of superabsorbent particles in coform fibrous webs. Conventional absorbent structures, such as those described above, however, have not provided desired combinations of total absorbent capacity, dimensional stability, high strengths, ease of manufactures, and low cost. For example, creped wading and tissues have low basis weight, and require a large number of plies to produce a desired level of absorbent capacity and/or total basis weight. Non-fiberized wood pulp board has excessive density and stiffness, while fiberized, airlaid wood pulp fluff has low strength and low dimensional stability. Typically, an airlaid fluff web is reinforced with a supplemental carrier layer, such as tissue, to enable its movement through the manufacturing process for the assembled absorbent article. A highly densified web of airlaid wood pulp fluff can have excessive stiffness and can include undesirable hard spots. In addition, the fluff web has been dimensionally unstable and has tended to grow in thickness whenever the fluff web is unconstrained. Airlaid coform webs can be constructed with a combination of natural and synthetic fibers to increase the web strength. The inclusion of synthetic fibers can, however, excessively raise the cost of the coform webs. Similarly, hydroentangled pulp webs typically require sufficient proportions of relatively long fibers, such as fibers of one-half inch (1.27 cm) or more in length, to generate the entangled web structures. The inclusion of the long fibers and the complexity of the hydroentangling process can excessively raise the cost of the formed fibrous webs.

As a result, there has been a continuing need for a low density, high strength fibrous web which can be produced low cost and can be suitable for use in selected articles, such as articles which may be absorbent and may be disposable. There has also been a continuing need for fibrous webs having desired parameters of high basis weight and low stiffness for use in the selected articles.

BRIEF DESCRIPTION OF THE INVENTION

The present invention provides an article having at least one absorbent fibrous web layer which is substantially non-hydroentangled. In particular aspects, the fibrous web layer has high a basis weight, a low density, and a high peak tensile strength. In other aspects, the fibrous web layer can also have a fiber content in which a large proportion of the fiber content are short fibers. In still further aspects, the fibrous web layer of the invention can be incorporated into an absorbent article comprising a backsheet layer, and a liquid permeable topsheet layer which is disposed in facing relation with the backsheet layer. An absorbent retention portion is interposed between the backsheet layer and the topsheet layer, and the retention portion has an overall absorbent capacity of at least about 300 gm of saline.

The present invention, in its various aspects, can advantageously provide a lower cost fibrous web which has relatively high tensile strength and high flexibility, and can provide desired levels of absorbency. The high web strength can allow the web to be more readily processed through a manufacturing line to form a final article. The high basis weight and flexibility of the web can help improve the function and utility of the web in selected articles, such as absorbent articles.

BRIEF DESCRIPTION OF THE DRAWINGS

The invention will be more fully understood and further advantages will become apparent when reference is made to the following detailed description and accompanying drawings in which:

FIG. 3 representatively shows a longitudinal cross-sectional view taken through an article of the type shown in FIG. 2;

FIG. 6 representatively shows a longitudinal cross-sectional view taken through an article of the type shown in FIG. 5;

FIG. 9A is a table which representatively shows particular physical characteristics of selected sample materials;

FIG. 9B is a continuation of the table in FIG. 9A;

FIG. 10A is a table which representatively shows additional physical and functional characteristics of the selected sample materials;

FIG. 10B is a continuation of the table in FIG. 10A;

FIG. 11 is a table which summarizes data pertaining to the geometric mean tensile strength values for particular sample materials;

DETAILED DESCRIPTION OF THE INVENTION

The structures of the present invention will be described herein in relationship to their use in disposable absorbent articles. For the purpose of the present invention, a disposable absorbent article is an article which absorbs and contains liquids, such as body exudates, and is intended to be discarded after a limited period of use. The articles are not intended to be laundered or otherwise restored for reuse. While the present description will particularly be made in the context of a disposable absorbent article, particularly a disposable diaper, it should be understood that the various structures of the present invention are also applicable to other articles, such as adult incontinence garments, sanitary napkins, children's training pants, bed pads, absorbent wipes and the like.

Figure 1:
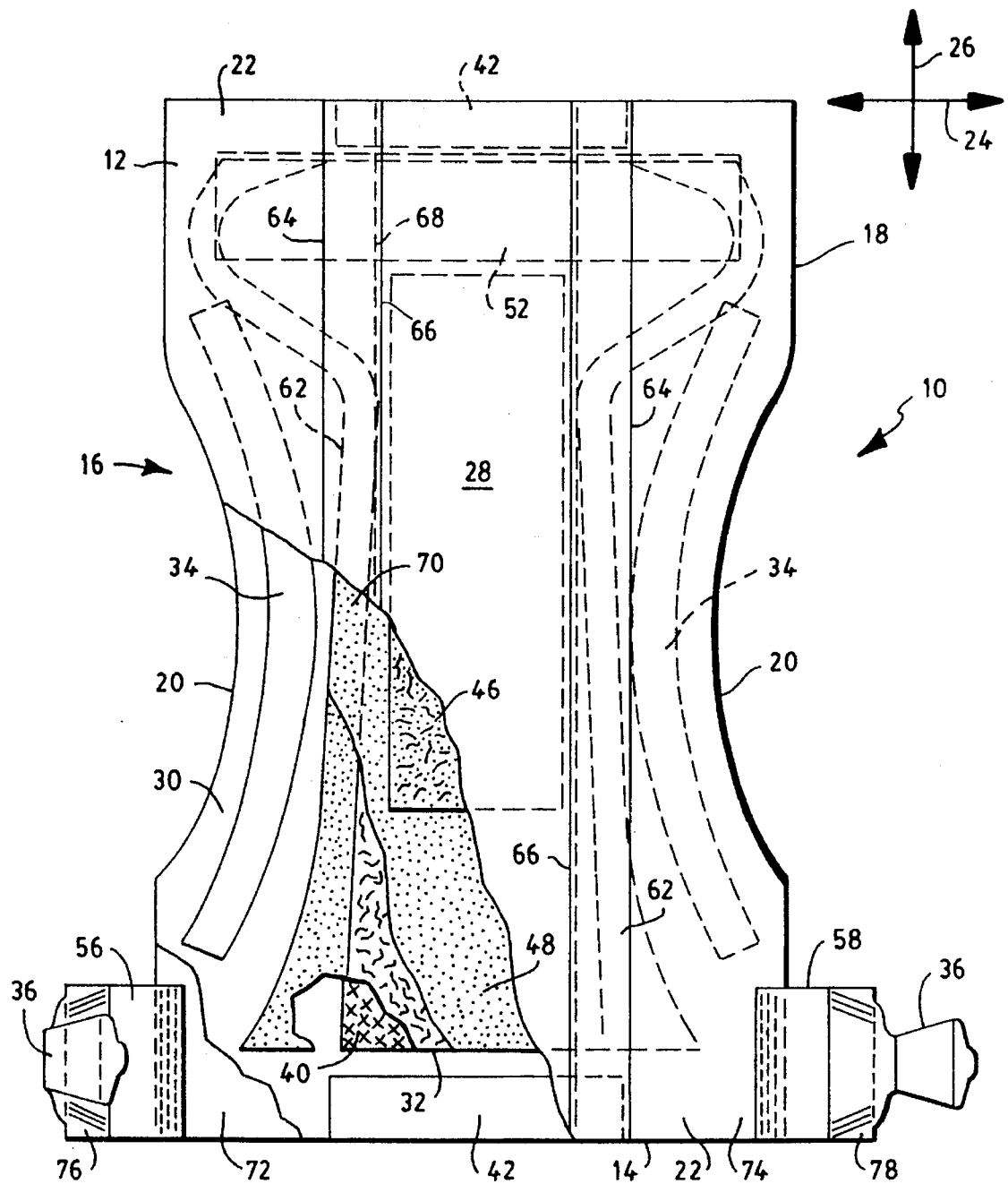
FIG. 1 shows a top view of a representative article of the invention.

With reference to FIG. 1, an article of the invention includes at least one fibrous web layer 40, which may include one or more types of fibers, such as hydrophilic fibers. The fibrous web layer can be absorbent, and the hydrophilic fibers can, for example, be composed of cellulosic fibers. The fibrous web layer 40 can have a high basis weight, such as a basis weight of at least about 60 gsm (grams per square meter), and can have a low density, such as a density of not more than about 0.25 gm/cc. The web layer can further have a high tensile strength, such as a peak geometric mean (GM) tensile strength of at least about 250 grams-force per centimeter of width of said fibrous web layer, and can have a fiber content in which a large proportion, such as at least about 90 wt %, of the fiber content are short fibers. The short fibers can have a fiber length of not more than about 0.4 inch (about 1 cm).

The fibrous web layer 40 is substantially non-hydroentangled. For example, the web layer can be composed of fibers which have been deposited out of an aqueous suspension in a substantially random fashion, and subsequently dried. The web layer is thereby formed substantially without orienting the fibers.

Particular aspects of the present invention can provide an absorbent article, such as the representatively shown diaper 10, which has a cross-wise, lateral dimension 24 and a length-wise, longitudinal dimension 26. The diaper 10 has a front waistband section 12, a rear or back waistband section 14, and an intermediate section 16 which interconnects the front and rear waistband sections. The article also includes a backsheet layer 30 which has a laterally extending width and a longitudinally extending length. A porous, liquid permeable topsheet layer 28 also has a laterally extending width and a longitudinally extending length, and is superposed in facing relation with the backsheet layer 30. An absorbent body, such as an absorbent structure 32, is interposed between the backsheet layer 30 and the topsheet layer 28, and the absorbent structure includes a retention portion 48. In particular aspects, the absorbent structure can have an overall basis weight of fibers which is at least about 300 grams per square meter (gsm), and in other aspects can have an overall absorbent capacity of at least about 400 grams of saline. In further aspects, the retention portion 48, by itself, can have an overall basis weight of fibers which is at least about 300 grams per square meter (gsm), and can have an overall absorbent capacity of at least about 400 grams of saline.

In particular arrangements, the fibrous web layer 40, can be employed to construct or otherwise provide one or more selected sections or components of the retention portion 48. Further arrangements of the fibrous web layer 40 can have a selected Gurley stiffness to thickness quotient. Where the stiffness is expressed in Standard Gurley Units, the Gurley stiffness to thickness quotient can be not more than about 2000 SGU/mm (Standard Gurley Units per millimeter). In other aspects, the fibrous web layer 40 can have a fiber content in which at least about 95 wt % of the fiber content are fibers having a fiber length of not more than about 1.2 inch (about 3 cm). Additional aspects of the invention can provide a fibrous layer 40 composed of a plurality of integrally formed, cooperating zones with different zones having different characteristics.

The various aspects of the fibrous web layer 40 of the invention can advantageously provide a low cost material having high bulk along with high strength and flexibility. The web layer can also have improved resistance to buckling, roping and twisting, and can be produced with lower cost manufacturing steps.

FIG. 1 representatively shows a plan view of the diaper 10 in its flat-out, uncontracted state (i.e., with all elastic induced gathering and contraction removed). Portions of the structure are partially cut away to more clearly show the interior construction of diaper 10, and the major facing surface of the diaper which contacts the wearer is facing the viewer. In the shown embodiment, diaper 10 has a front waistband region 12, a back waistband region 14, an intermediate crotch region 16 which interconnects the front and rear waistband regions. The outer edges of the diaper define a periphery 18 in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear. The diaper additionally has a transversely extending, lateral width dimension 24 and a longitudinal, length dimension 26.

Diaper 10 typically includes a porous, liquid permeable topsheet 28; a substantially liquid impermeable backsheet 30; an absorbent structure 32, positioned between the topsheet and backsheet; a surge management portion 46; and elastic members, such as leg elastics 34 and waist elastics 42. The surge management portion is positioned in liquid communication with the absorbent structure, and the absorbent structure includes a retention portion 48. Topsheet 28, backsheet 30, absorbent structure 32, surge management portion 46 and the elastic members 34 and 42 may be assembled in a variety of well-known diaper configurations. In addition, the diaper can include a system of containment flaps 62, a system of side panel members 56 and 58, and suitable fastening means, such as provided by fastener tabs 36. An elasticized side panel can be connected to the article at each laterally opposed end region 72 and 74 of at least one of the front and rear waistband sections. The side panels 56 and 58 are constructed to be elastically stretchable at least along a laterally extending cross-direction 24 of the article, and the fastening means, such as provided by the tape tab fasteners 36, is configured for securing the article on a wearer. A tab fastener connects to a laterally distal end region of at least one, and desirably both, of the side panels. In the illustrated embodiment, for example, a first tape tab fastener 36 is connected to the distal end region 76 of side panel 56, and a second tape tab fastener is connected to the distal end region 78 of elasticized side panel 58.

As representatively shown, topsheet 28 and backsheet 30 may be generally coextensive, and may have length and width dimensions which are generally larger than the corresponding dimensions of the absorbent structure 32. Topsheet 28 is associated with and superimposed on backsheet 30, thereby defining the periphery 18 of diaper 10. The periphery delimits the outer perimeter of the diaper 10, and in the illustrated embodiment, comprises laterally marginal end edges 22, and contoured longitudinally extending marginal side edges 20. The diaper 10 has front and back waistband regions 12 and 14, respectively, extending from the laterally extending end edges 22 of diaper periphery 18 toward the transverse center line of the diaper along a distance of from about 2 percent to about 10 percent of the overall length of diaper 10. The waistband regions comprise those upper portions of diaper 10, which when worn, wholly or partially cover or encircle the waist or mid-lower torso of the wearer. The intermediate region 16 lies between and interconnects waistband regions 12 and 14, and comprises that portion of diaper 10 which, when worn, is positioned in the crotch region between the legs of the wearer and covers the lower torso of the wearer. Thus, the intermediate region 16 is an area where repeated fluid surges typically occur in the diaper or other disposable absorbent article.

Topsheet 28 presents a body-facing surface which is compliant, soft-feeling, and non-irritating to the wearer's skin. Further, topsheet 28 can be less hydrophilic than retention portion 48, and is sufficiently porous to be liquid permeable, permitting liquid to penetrate through its thickness.

A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, for example, topsheet 28 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant or wetting agent, such as about 0.28% Triton X-102 surfactant. The surfactant can be applied by any conventional means, such as spraying, printing, brush coating or the like.

The surfactant material can be applied to a medial section of the topsheet layer 28 to provide a greater wettability of the medial section, as compared to a remainder of the topsheet layer 28. In particular configurations, the cross-directional width of the surfactant-treated medial section can be substantially equal to or less than the cross-directional width of the surge management portion 46. The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The various configurations of the invention can include elasticized containment flaps 62. The representatively shown configuration includes two containment flaps 62 which may, for example, be connected to the bodyside surface of topsheet layer 28. Suitable constructions and arrangements for containment flaps 62 are described, for example, in U.S. Pat. No. 4,704,116 issued Nov. 3, 1987, to K. Enloe, the entire disclosure of which is hereby incorporated by reference in a manner that is consistent (not contradictory) herewith. Other configurations of the containment flaps 62 are described in U.S. patent application Ser. No. 208,816 of R. Everett et al., filed Mar. 4, 1994 and entitled ABSORBENT ARTICLE HAVING AN IMPROVED SURGE MANAGEMENT (Attorney docket No. 11,375), the entire disclosure of which is hereby incorporated by reference in a manner that is consistent herewith.

The containment flaps can be attached to topsheet layer 28 along length-wise extending fixed regions, such as fixed edges 64, of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In particular embodiments, for example, the moveable edge of the barrier flap is connected to the flap elastics by partially doubling the flap material back upon itself by a limited amount which is sufficient to enclose the flap elastics 68.

At least a pair of containment or barrier flaps 62 can be connected to appointed, laterally opposed, longitudinally extending regions of the topsheet layer 28, and the connected topsheet regions can be located generally adjacent to the laterally opposed side edge regions of the medial section of the topsheet layer. The connected topsheet regions can be located substantially laterally inboard of the elasticized side margins of the diaper article 10. Optionally, the containment flaps can be connected to the diaper at regions which are located outboard of the leg elastics.

The containment flaps may, for example, be constructed of a fibrous material which is similar to the material comprising topsheet 28, or similar to the material comprising surge management portion 46. Other conventional materials, such as polymer films, may also be employed. In other aspects of the invention, barrier flaps 62 are constructed of a material which is permeable to gas, such as ambient air. Alternative configurations of the invention can include barrier flaps which are constructed of a material which is resistant to a passage of aqueous liquid, such as urine, therethrough. For example, barrier flaps 62 may be constructed of a spunbond-meltblown-spunbond (SMS) laminate material. For example, the barrier flaps can be constructed of a SMS material having a basis weight of about 0.85 osy (about 28 gsm). The spunbond layers can be composed of polypropylene fibers, and the meltblown layer is composed of meltblown polypropylene fibers.

In the various configurations of the invention, such as where the barrier flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. In the present specification, the term "flexible" refers to materials which are compliant and which will readily conform to the general shape and contours of the wearer's body. Backsheet 30 typically helps to prevent the exudates contained in absorbent structure 32 from wetting articles such as bedsheets and overgarments which contact diaper 10.

In particular embodiments, the backsheet 30 is a polyethylene film having a thickness of from about 0.012 millimeters (0.5 mil) to about 0.051 millimeters (2.0 mils). In particular embodiments, the backsheet can be a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 30 typically provides the outer cover of the article. Optionally, however, the article may include a separate outer cover member which is in addition to the backsheet.

Backsheet 30 may optionally be composed of a microporous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XK0-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance to provide side margins. The topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive or other bonds may be used to affix topsheet 28 to backsheet 30. It should be readily appreciated that the above-described types of attachment means may also be employed to interconnect and assemble together the various other component parts of the final, constructed article.

In the representatively shown embodiment of the invention, the topsheet layer 28 is disposed and secured in facing relation with the backsheet layer 30 to retain and hold the retention portion 48 and the surge management portion 46 between the backsheet layer and the topsheet layer. The marginal side regions of topsheet layer 28 can, for example, be operably connected to corresponding marginal side regions of the backsheet layer 30. Each of the attached marginal side regions of the topsheet and backsheet layers is located laterally outboard of its corresponding, associated side edge region of the surge management portion 46. Similarly, the topsheet 28 and/or backsheet 30 can include marginal end regions which are be located longitudinally outboard of the end edge regions of the retention portion 48 and/or surge management portion 46.

In the representatively shown arrangement, the elastic members 34 are disposed adjacent the periphery 18 of diaper 10 along each of the longitudinal side edges 20 to provide elasticized leg openings. The leg elastic members 34 can be connected to either or both of the topsheet and backsheet layers to provide elasticized side margins of the diaper article, and can be arranged to draw and hold diaper 10 against the legs of the wearer. Waist elastic members 42 may also be disposed adjacent either or both of the end edges of diaper 10 to provide elasticized waistbands.

The elastic members 34 and 42 are secured to diaper 10 in an elastically contractible condition so that in a normal under-strain configuration, the elastic members effectively contract against diaper 10. The elastic members can be secured in an elastically contractible condition in at least two ways. For example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In example of the illustrated configuration, leg elastic members 34 extend essentially along the complete length of the crotch region of the diaper 10. Alternatively, elastic members 34 may extend the entire length of diaper 10, or any other length suitable providing the arrangement of elastically contractible lines desired for the particular diaper design.

The elastic members 34 and 42 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using any of a variety of bonding patterns, or may be adhesively bonded to diaper 10 with sprayed or swirled patterns of hotmelt or other type of adhesive.

The leg elastic members 34 may, for example, comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA (trademark) elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned inboard from the outer most edge of the set of elastic strands. The curved elastics may optionally have an inwardly bowed and outwardly bowed, reflex-type of curvature. In particular arrangements, the curvature of the elastics may not be configured or positioned symmetrically relative to the lateral centerline of the diaper. Accordingly, the length-wise center of the elastics may be offset by a selected distance toward either the front or rear waistband of the diaper to provide desired fit and appearance.

An absorbent body, such as provided by absorbent structure 32, is typically positioned between topsheet 28 and backsheet 30. The absorbent body has a construction which is generally compressible, conformable, non-irritating to the wearer's skin, and capable of absorbing and retaining liquid body exudates, such as urine. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or plies, or may be configured with other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

The absorbent structure 32 may be manufactured in a wide variety of sizes and shapes (for example, rectangular, trapezoidal, T-shape, I-shape, hourglass shape, etc.) and may include a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, the densities and/or basis weights of the respective surge management 46 and retention 48 portions, as well as their relative ratios, can be varied to meet particular performance requirements.

In a particular aspect of the invention, the absorbent structure has an absorbent capacity of at least about 300 gm of synthetic urine. Alternatively, the absorbent structure can have an absorbent capacity of at least about 400 gm of synthetic urine, and optionally can have an absorbent capacity of at least about 500 gm of synthetic urine to provide improved performance.

Various types of wettable, hydrophilic fibrous material can be used to form the component parts of the absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. It is also contemplated that selected blends of the various types of fibers mentioned above may also be employed.

In the present description, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

The retention portion 48 can include selected quantities of high-absorbency material, and the high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly-(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

The high-absorbency material used in the retention portion 48 can be in the form of discrete particles. The particles can be of any desired shape, for example, spiral or semispiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the retention portion 48.

Preferred for use are particles having an average particle size of from about 20 micrometers to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byefly et al., entitled "ABSORBENT COMPOSITES AND ABSORBENT ARTICLES CONTAINING SAME" and filed on Sep. 11, 1991 (Attorney Docket No. 10,174), the entire disclosure of which is hereby incorporated by reference in a manner that is consistent with the present specification.

In a particular aspect of the invention, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled "ABSORBENT PRODUCTS CONTAINING HYDROGELS WITH ABILITY TO SWELL AGAINST PRESSURE" (Attorney Docket No. 8786); European Patent Application EP 0 339 461A1, published Nov. 2, 1989; the entire disclosure of which is hereby incorporated by reference in a manner that is consistent with the present specification. An example of a superabsorbent polymer suitable for use in the present invention is SAN-WET IM 3900 polymer available from Hoechst Celanese, a business having offices in Portsmouth, Va. Other suitable superabsorbents may include W45926 polymer obtained from Stockhausen, a business having offices in Greensboro, N.C.

Due to the desired thinness of the retention portions 48, and/or the high superabsorbent concentrations within the retention portion, the liquid uptake rates of the retention portion, by itself, may be too low, or may not be adequately sustained over three insults of liquid into the absorbent structure. The addition of a porous, liquid-permeable portion of surge management material, however, can advantageously improve the overall uptake rate of the composite absorbent structure. The surge management portion 46 may be less hydrophilic than the retention portions 48, and has an operable level of density and basis weight to quickly collect and temporarily hold liquid surges, to transport the liquid from its initial entrance point and to substantially completely release the liquid to other parts of the absorbent structure 32, particularly the retention portions 48. This configuration can help prevent the liquid from pooling and collecting on the portion of the absorbent garment positioned against the wearer's skin, thereby reducing the feeling of wetness by the wearer.

Various woven and nonwoven fabrics can be used to construct the surge management portion 46. For example, the surge management portion may be a layer composed of a meltblown web or a spunbonded web of polyolefin fibers. The surge management layer may also be a bonded-carded-web or an airlaid web composed of natural or synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch (about 2.54–7.6 cm). The surge management portion may be composed of a substantially hydrophobic material, and the hydrophobic material may optionally be treated with a surfactant or otherwise processed to impart a desired level of wettability and hydrophilicity.

The surge management portion 46 is typically arranged in a direct, contacting liquid communication with an adjacent absorbent retention portion 48. As representatively shown, the surge management portion 46 may be configured for placement adjacent a major, outwardly facing, outerside surface of the topsheet 28. Optionally, the surge management portion can be placed adjacent an inwardly facing, bodyside surface of topsheet layer 28. The shown configuration of the surge management portion is operably connected to the topsheet layer with a conventional attaching mechanism, such as a swirl adhesive pattern. Similarly, the surge management portion can be operably connected to the bodyside layer of wrapsheet 70. The amount of adhesive add-on should be sufficient to provide the desired levels of bonding, but should be low enough to avoid excessively restricting the movement of liquid from the topsheet layer, through the surge management portion and into the retention portion.

In the various configurations of the invention, the retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. The surge management portion 46 may, however, contain a very small amount of particulate gelling material to help acquire an initial liquid surge, but the amount should not be excessive. Excessive amounts of particulate absorbent gelling material can cause the structure to retain and hold unacceptably high amounts of the liquid and can impair the transport of liquids into the retention portion 48.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length occupied by retention portion 48, or may extend over only a part of the overall retention portion length. Where the surge management portion extends only partially along the overall length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the terminal end edges of the overall retention portion. In particular configurations of the invention, the corresponding, relatively adjacent front end edge of surge management portion 46 can be spaced a predetermined discrete distance from a front waistband end edge of the overall retention portion.

It has been found that an effective fabric for constructing the surge management portion can be distinctively characterized by particular parameters; such as basis weight, permeability, specific volume, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the entire disclosures of which are hereby incorporated by reference in a manner that is consistent herewith.

To ensure a rapid intake of liquid, the overall structure of the surge portion 46 has hydrophilic tendencies. At least a portion of the fibers have a contact angle less than 90 degrees to provide a fibrous nonwoven web which has sufficient hydrophilic tendencies when the web has a saturation capacity greater than 55 grams of 0.9% saline solution per gram of web.

Another feature of the surge material is its resiliency in both the wet and dry states. The surge material is configured to rapidly acquire a large amount of liquid without excessive collapsing. Excessive collapse would be detrimental since the collapsing of the surge material would result in a reduced capacity for retaining liquid. Accordingly the surge materials employed with the present invention have a wet resilience which allows them to substantially retain their bulk in both the wet and dry states.

In the shown configuration of the diaper 10, the side panel members 56 and 58 are separate members operably connected and attached to laterally opposed end sections of the back waistband portion of backsheet 30. The side panels can be composed of a substantially non-elastomeric material, such as polymer films, woven fabrics, nonwoven fabrics or the like, as well as combinations thereof. In particular aspects of the invention, the side panels can be composed of a substantially elastomeric material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European patent application EP No. 0 110 010 published on Apr. 8, 1987 with the inventors listed as J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

The fastening system, such as provided by the tab fasteners 36, is typically applied to the back waistband region 14 of diaper 10 to provide a mechanism for holding the diaper on the wearer. The tab fasteners 36 can be any of those well known in the art, and are typically applied to the corners of diaper 10. For example, adhesive fasteners, mechanical fasteners, hook and loop fasteners, snaps, pins or buckles, may be used alone, or in combination. In the shown configuration, the fasteners are adhesive fasteners, which are constructed to releasably adhere to a landing zone patch 52 attached to the front waistband section of the diaper to provide a refastenable adhesive fastening system. More particularly, the fastener tabs 36 connect to associated, laterally outboard edge regions of the side panels 56 and 58 along an appointed factory-bond region of the tab fasteners. In particular aspects of the invention, the fastener tabs can have a relatively wide user-bond section in combination with a relatively narrower intermediate section. The intermediate section is positioned between the user-bond and factory-bond sections of the fastener tab.

Articles which include elastomeric side panels and distinctively configured fasteners are described in U.S. patent application Ser. No. 168,615 of T. Roessler et al., entitled DYNAMIC FITTING DIAPER and filed Dec. 16, 1993 (Attorney docket No. 10,961), and U.S. patent application Ser. No. 366,080 of G. Zehner et al., filed Dec. 28, 1994, and entitled HIGH-PEEL TAB FASTENER (attorney docket No. 11,571), the entire disclosures of which are hereby incorporated herein by reference in a manner that is consistent herewith. The fastening systems can include a stress beam member for distributing applied stresses the area of the side panel material, and can include fastening tabs which incorporate a necked down intermediate region in combination with a relatively wider, user-bond section thereof.

Techniques for forming the desired fastening systems are described in U.S. patent application Ser. No. 200,593 of T. Roessler et al., entitled METHOD FOR MAKING A FASTENING SYSTEM FOR A DYNAMIC FITTING DIAPER and filed Feb. 23, 1994 (Attorney docket No. 11,186), the entire disclosure of which is hereby incorporated herein by reference in a manner that is consistent herewith.

The fibrous web layer 40 employed in the present invention can be composed of a fibrous material which is substantially non-hydroentangled. The web layer 40 can have desired levels of bulk, flexibility and strength without undergoing the complicated procedures of hydroentanglement and its associated post-treatments, such as further drying. In particular aspects of the invention, the fibrous web layer 40 can have a basis weight of at least about 60 gsm. The fibrous web layer 40 can alternatively have a basis weight of at least about 100 gsm, and can optionally have a basis weight of at least about 125 gsm to provide desired levels of performance.

In other aspects of the invention, the fibrous web layer 40 can have a relatively low density to improve the flexibility and/or absorption characteristics of the web. For example, the web layer 40 can have a density of not more than about 0.25 gm/cc. Alternatively, the web layer density can be not more than about 0.23 gm/cc, and optionally can be not more than about 0.2 gm/cc to provide improved performance. In addition, the web layer density can be as low as 0.1 gm/cc, and optionally, can be as low as 0.05 gm/cc.

The fibrous web layer 40 can also have a high strength which can, for example, allow the web layer to be processed through a conventional manufacturing line substantially without the need for supplemental reinforcement or carrier layers. In particular configurations of the invention, the web layer 40 can have a peak geometric mean tensile strength of at least about 250 grams-force per centimeter of width of said fibrous web layer. The web layer 40 can alternatively have a peak geometric mean tensile strength of at least about 300 grams-force per centimeter of width, and can optionally have a peak geometric mean tensile strength of at least about 350 grams-force per centimeter of width. In further arrangements, the web layer 40 can have a peak geometric mean tensile strength which is as high as about 2500 grams-force per centimeter of width, and optionally, can have a peak geometric mean tensile strength which is as high as about 5000 grams-force per centimeter of width. A suitable technique for determining the geometric mean tensile strength is described below in the "EXAMPLES".

The large proportion of short fibers in the fibrous web layer 40 can provide for various advantages, such as keeping the cost of the web low and permitting a higher processing speed. In particular aspects of the invention, the web layer 40 has a fiber content in which at least about 90wt % of the fiber content are fibers having a fiber length of not more than about 0.4 inch (about 1 cm). Alternatively, at least about 95 wt %, and optionally, at least about 98 wt % of the fiber content are fibers having a fiber length of not more than about 0.4 inch (about 1 cm). In other desired arrangements, the web layer 40 can have a fiber content in which substantially about 100 wt % of the fiber content are fibers having a fiber length of not more than about 0.4 inch (about 1 cm).

To further help the efficiency and cost effectiveness of the fibrous web layer 40, the web layer can have a fiber content in which not more than about 5 weight percent of the fiber content are fibers having a fiber length of at least about 1.2 inch (about 3 cm). Alternatively, not more than about 2 weight percent of the fiber content, and optionally, substantially zero weight percent of the fiber content are fibers having a fiber length of at least 1.2 inch (about 3 cm).

To provide an article which is readily conformable to the body of the wearer, the fibrous web layer 40 can be constructed to have a Gurley stiffness of not more than about 10,000 SGU. Alternatively, the Gurley stiffness can be not more than about 5,000 SGU, and optionally can be not more than about 2,000 SGU to provide desired levels of performance. In other aspects of the invention, the fibrous web layer 40 can be constructed to have a Gurley stiffness of not less than about 100 SGU. Alternatively, the Gurley stiffness can be not less than about 150 SGU, and optionally can be not less than about 200 SGU to provide other aspects of improved performance.

In other aspects of the invention, the fibrous web layer 40 can be configured to have a Gurley stiffness to thickness quotient of not more than about 4,000 SGU/mm. The web layer 40 can be further constructed to have a Gurley stiffness to thickness quotient which is alternatively not more than about 2,000 SGU/mm, and optionally is not more than about 1,000 SGU/mm to provide improved levels of flexibility and conformability.

A suitable technique for determining the Gurley stiffness is set forth in TAPPI T 543. For the purposes of the present invention, the stiffness values are measured and expressed in terms of Standard Gurley Units (SGU) (traditionally reported as milligrams of force).

In the various configurations of the invention, the fibrous web layer 40 can advantageously provide relatively high levels of tensile strength without employing large amounts of supplemental binder material, such as binder fiber. In particular aspects of the invention, the fibrous web layer 40 is substantially free of binder material. Alternatively, the fibrous web layer can include not more than about 1.5 weight percent of binder material, and optionally can include not more than about 5 weight percent of binder material.

The fibrous web layer 40 can be substantially free of superabsorbent polymer material, and can be composed of cellulose fibers which are primarily hydrogen bonded to one another. Desired configurations of the fibrous web layer 40 can be composed of at least about 95 weight percent of cellulosic fibers. Alternatively, the fiber web can be composed of substantially 100 weight percent of cellulosic fibers. The bonding between the fibers within the web layer is in large proportion provided by hydrogen bonding. In particularly desired arrangements, at least about 95 percent of the bonding is provided by hydrogen bonding. In other desired arrangements, at least about 98 percent, and desirably substantially 100 percent of the bonding is provided by hydrogen bonding.

In other aspects of the invention, the fibrous web layer 40 is non-hydroentangled, and is substantially free of fused bonds, such as thermal bonding. Desirably, not more than about 15% of the interfiber bonding within the fibrous web 40 is provided by fused bonds. Alternatively, not more than about 5%, and optionally not more than about 1% of the interfiber bonding is provided by fused bonds.

In desired arrangements of the invention, the fibrous web layer 40 includes substantially no added or supplemental chemical bonding agents. In other aspects of the invention, the fibrous web layer 40 can include a selected quantity of an added chemical bonding agent, such as bonding agents composed of vinyl acrylic copolymers, polyvinyl acetate, cross-linkable polyamides, polyvinyl alcohol, and the like. In particular configurations, the fibrous layer 40 can contain not more than about 5 wt %, and optionally, can contain not more than about 2 wt % of the chemical bonding agent to provided desired benefits. If the amount of the chemical bonding agent is too large, the fibrous web can undesirably exhibit excessive cost, increased processing complexity, decreased absorption rates, decreased softness and decreased flexibility.

The fibrous web layer 40 is an integral, unitary fibrous web which, in particular aspects, has a web thickness of at least about 0.5 mm. Alternatively, web thickness is at least about 0.6 mm, and optionally is at least about 0.7 mm to provide desired benefits. In addition, the fibrous web layer can have a web thickness of not more than about 4 mm. Alternatively, the layer thickness can be not more than about 3.6 mm, and optionally can be not more than about 2.8 mm to provide desired performance. For the purpose of the present invention, the thickness of the fibrous web layer is determined under a restraining pressure of 0.2 psi (1.4 kPa).

The fibrous layer 40 of the invention can be composed of a plurality of integrally formed, cooperating zones with different zones configured to have different characteristics. The zones extend substantially along the general plane of the fibrous layer, and the differing zones can provide differing, selected physical attributes through the thickness of the fibrous layer 40. For example, the fibrous layer 40 of the invention can include a relatively high-density core zone integrated into a sandwich arrangement between two, relatively lower-density zones, wherein the lower-density zones have a higher loft and zone thickness than the high-density zone. The high-density zone can impart desired levels of strength, such as higher geometric mean tensile strength, and other properties, such as desired levels of capillary wicking. The lower-density zones can impart desired levels of bulk and void volume. The resultant, integral composite structure can be formed from a single, unitary base layer at lower cost and higher efficiencies.

In particular configurations of the invention, the fibrous web layer 40 can be composed of a fibrous web material which has been mechanically worked or otherwise treated to impart a distinctive combination of strength, flexibility and high basis weight, as well as other selected characteristics. The fibrous material can be subjected to a treatment which imparts a multiplicity of localized, miniature areas of mechanical strain, and in particular configurations of the invention, the fibrous web layer 40 can be subjected to a mechanical treatment which imparts a predetermined pattern of locally strained areas distributed over the area of the fibrous web layer. Localized tensile stresses applied to the fibrous layer can thereby produce miniature strains, such as miniature bond fractures or miniature compacted areas, within the treated fibrous web. The strains can impart desired levels of softness and flexibility to the web, and can be produced while substantially avoiding a fiberization or fragmentation of the web.

The web layer 40 can, for example, be provided by a fibrous, mechanically worked, cellulosic material, and the material may be referred to as microstrained pulp. A suitable technique for producing the microstrained pulp is described in U.S. patent application Ser. No. 259,824 filed Jun. 15, 1994 by R. Kamps et al. and entitled METHOD FOR MAKING SOFT TISSUE (Attorney docket No. 10939.1), the entire disclosure of which is hereby incorporated by reference in a manner that is consistent herewith.

Figure 2:
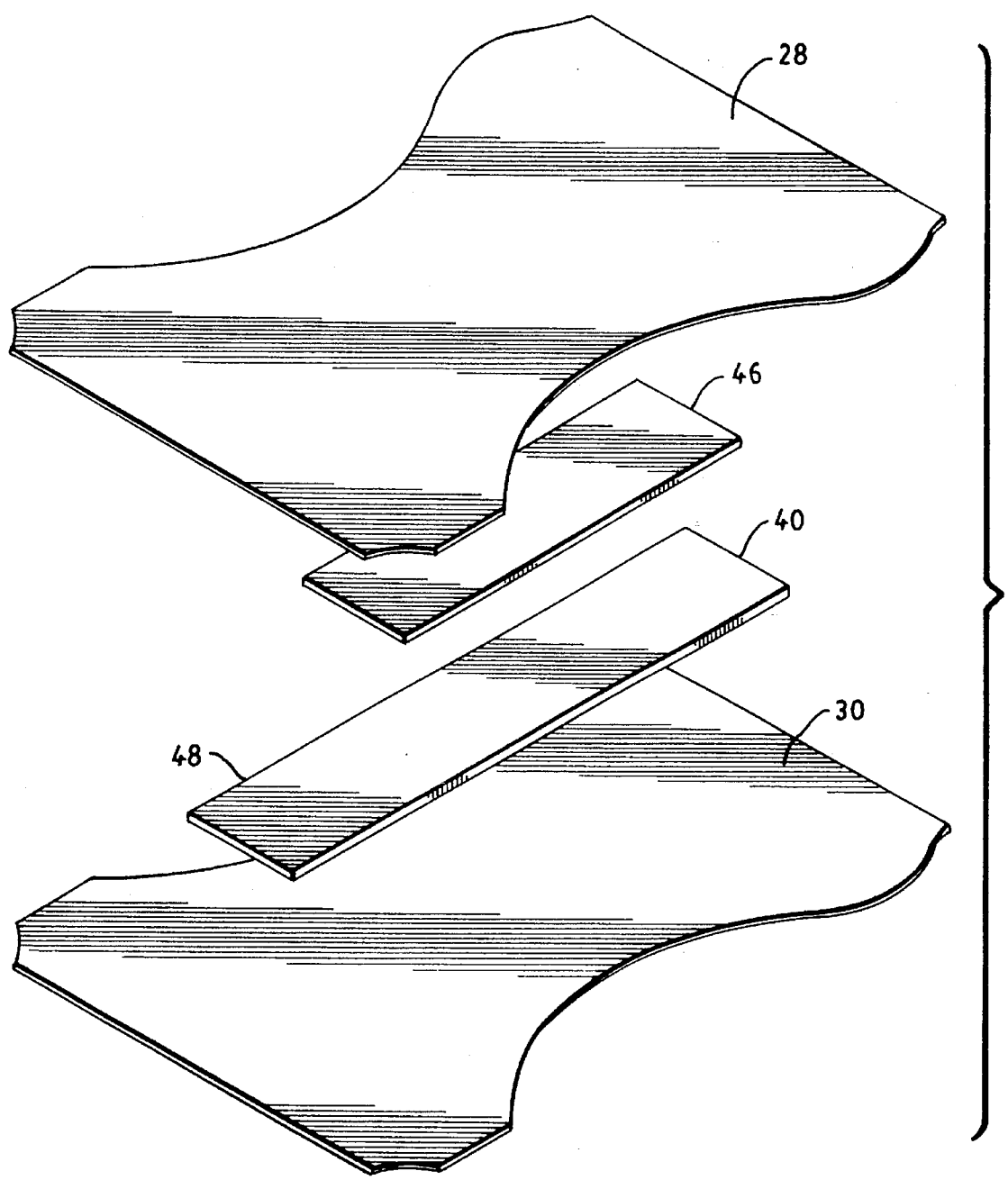
FIG. 2 representatively shows a perspective, expanded view of an article of the invention having a retention portion composed of one or more plies of the fibrous web layer of the invention.

With reference to FIGS. 2 and 3, particular aspects of the absorbent article of the present invention can have a retention portion 48 which includes one or more individual layers or plies of the fibrous web layer 40. The fibrous web layer or layers can be arranged to provide a composite basis weight within the range of about 120–1200 gsm. In particular aspects of the invention, where the retention portion includes multiple plies of the fibrous web layer 40, the individual plies can be configured with different characteristics, such as a selected combination of strength and/or absorbency characteristics. For example, different plies of the web layer 40 can have a different ply basis weight, ply density and/or ply tensile strength. The different plies can be adjacently located, or separated apart by intervening components (e.g. FIG. 5). As a result, as one moves through the thickness of the composite retention portion, the individual plies can contribute different absorbency characteristics and different tensile strength characteristics at their various locations within the absorbent structure.

Figure 4:
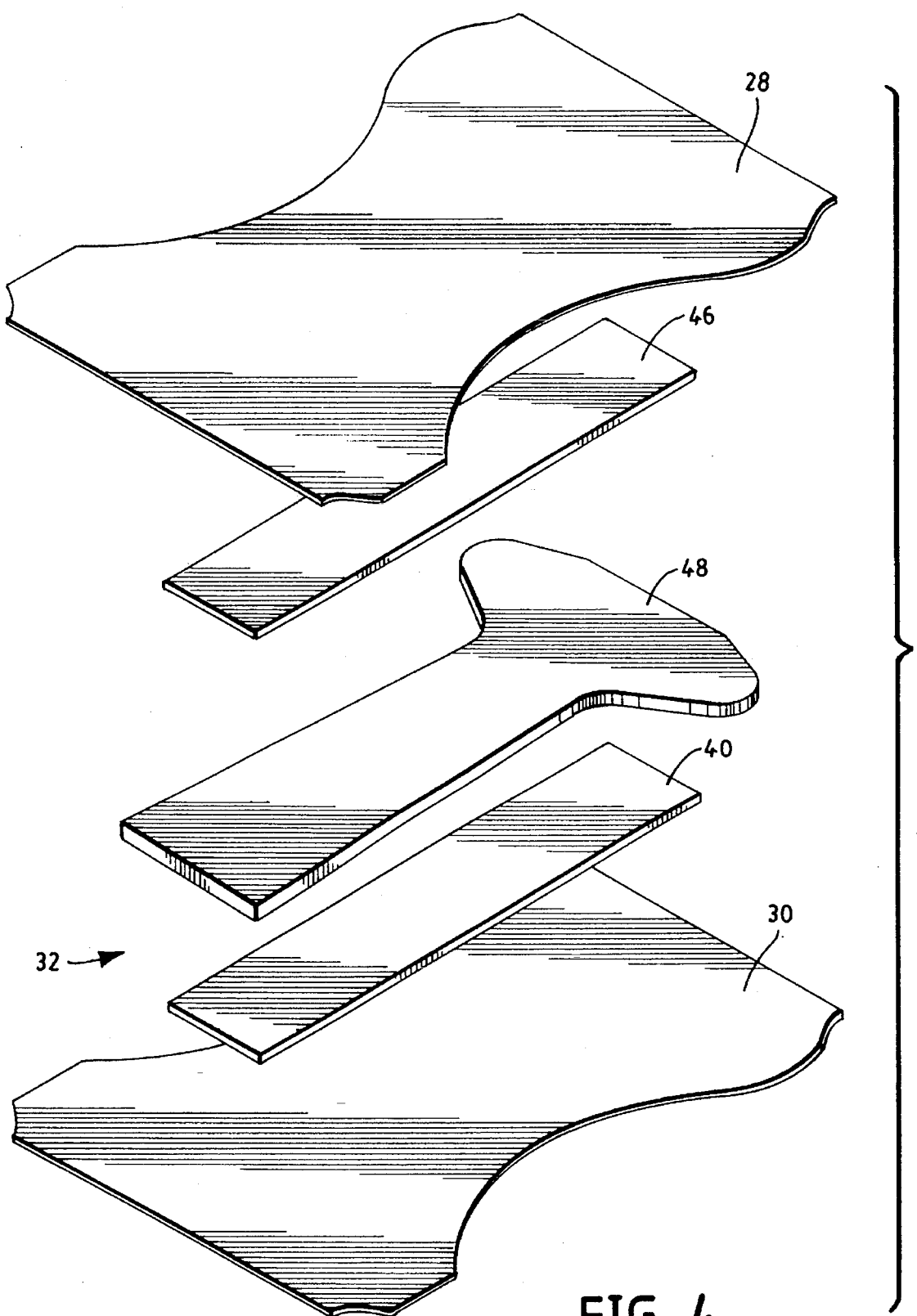
FIG. 4 representatively shows a perspective, expanded view of an article of the invention having a retention portion which includes an absorbent body composed of a mixture of woodpulp fluff fibers and superabsorbent particles.

With reference to FIG. 4, the retention portion 48 can alternatively comprise a mixture of hydrophilic fibers and high-absorbency particles, and a fibrous web layer 40 can be positioned adjacent either or both of the major facing surfaces of the retention portion 48. In the illustrated example, the fibrous web 40 is located on the outerside surface of the retention portion and the retention portion is composed of a mixture of cellulose wood pulp fibers and superabsorbent particles. In other arrangements, the retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers.

The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of the retention portion 48 which extends along the length dimension of the retention portion and can measure about 3.5–4.5 inches (about 8.9–11.4 cm) in width. In addition, the superabsorbent material may have a selected zoned placement to reduce the amount of superabsorbent material located proximate the side and end edges of the retention portion 48. The reduced amounts of superabsorbent material at the edges of the retention portion can improve the containment of the superabsorbent particles within the fibrous fluff matrix of the retention portion. The pulsed, zoned placement of the superabsorbent material can, for example, be achieved by the method and apparatus described in U.S. Pat. No. 5,028,224 to C. Pieper et al., entitled "METHOD AND APPARATUS FOR INTERMITTENTLY DEPOSITING PARTICULATE MATERIAL IN A SUBSTRATE" and issued Jul. 2, 1991 (Attorney Docket No. 8761), the entire disclosure of which is hereby incorporated by reference in a manner that is consistent herewith.

The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, alternatively is not less than about 30:70, and optionally is not less than about 45:55, by weight. Such fiber-to-particle ratios can be particularly desireable in the target zone of the absorbent structure.

The hydrophilic fibers and high-absorbency particles can form an average composite basis weight which is within the range of about 200–900 gsm. Again, such basis weight is particularly desireable in the target zone of the absorbent structure. In certain aspects of the invention, the average composite basis weight can be within the range of about 300–800 gsm, and optionally can be within the range of about 400–750 gsm to provide desired performance.

Due to the high concentrations of superabsorbent particles, or other high-absorbency material, in the retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an overwrap, such as wrap sheet 70, placed immediately adjacent and around the retention portion 48, as representatively shown in FIG. 1. The overwrap can include a hydrophilic high wet-strength envelope web, such as a high wet strength tissue or a synthetic fibrous web. Such overwrapping can also increase the in-use integrity of the absorbent structure. The wrap sheet can be suitably bonded, such as with adhesive, to the absorbent structure 32 and other components of the product construction, as desired.

The wrap sheet is preferably a layer of liquid permeable material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion 48, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion 48 at the waistband regions of the article.

The wrap sheet 70 may optionally include a multi-element wrapsheet which includes a separate bodyside wrap layer and a separate outerside wrap layer, each of which extends past all or some of the peripheral edges of the retention portion 48. Such a configuration of the wrap sheet can, for example, facilitate the formation of a substantially complete sealing and closure around the peripheral edges of retention portion 48, and can help add opacity and strength to the final article. In the illustrated embodiment, the bodyside and outerside layers of absorbent wrap 70 extend beyond the peripheral edges of the retention portion 48 to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. To provide the bonding between the bodyside and outerside portions of absorbent wrap 70, an adhesive, such as National Starch 33-9156 adhesive, can be printed onto the appointed bonding areas of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. The retention portion 48 can then be placed between the bodyside and outerside portions of absorbent wrap 70, and the mating edges of the absorbent wrap portions can be bonded together to provide a generally complete peripheral seal along substantially the entire perimeter of the retention portion 48. In the illustrated embodiment, the adhesive is applied at an add-on rate of about 5 grams of solids per square meter of bonding to attach together the lapping edges of the bodyside and outerside portions of absorbent wrap 70.

Alternative arrangements can have an absorbent wrap composed of a nonwoven meltblown fibrous web. The peripheral sealing of the bodyside and outerside wrap layers composed of meltblown webs may be accomplished by employing hot calendering to provide a sealed strip region around the periphery of the retention portion 48.

Figure 5:
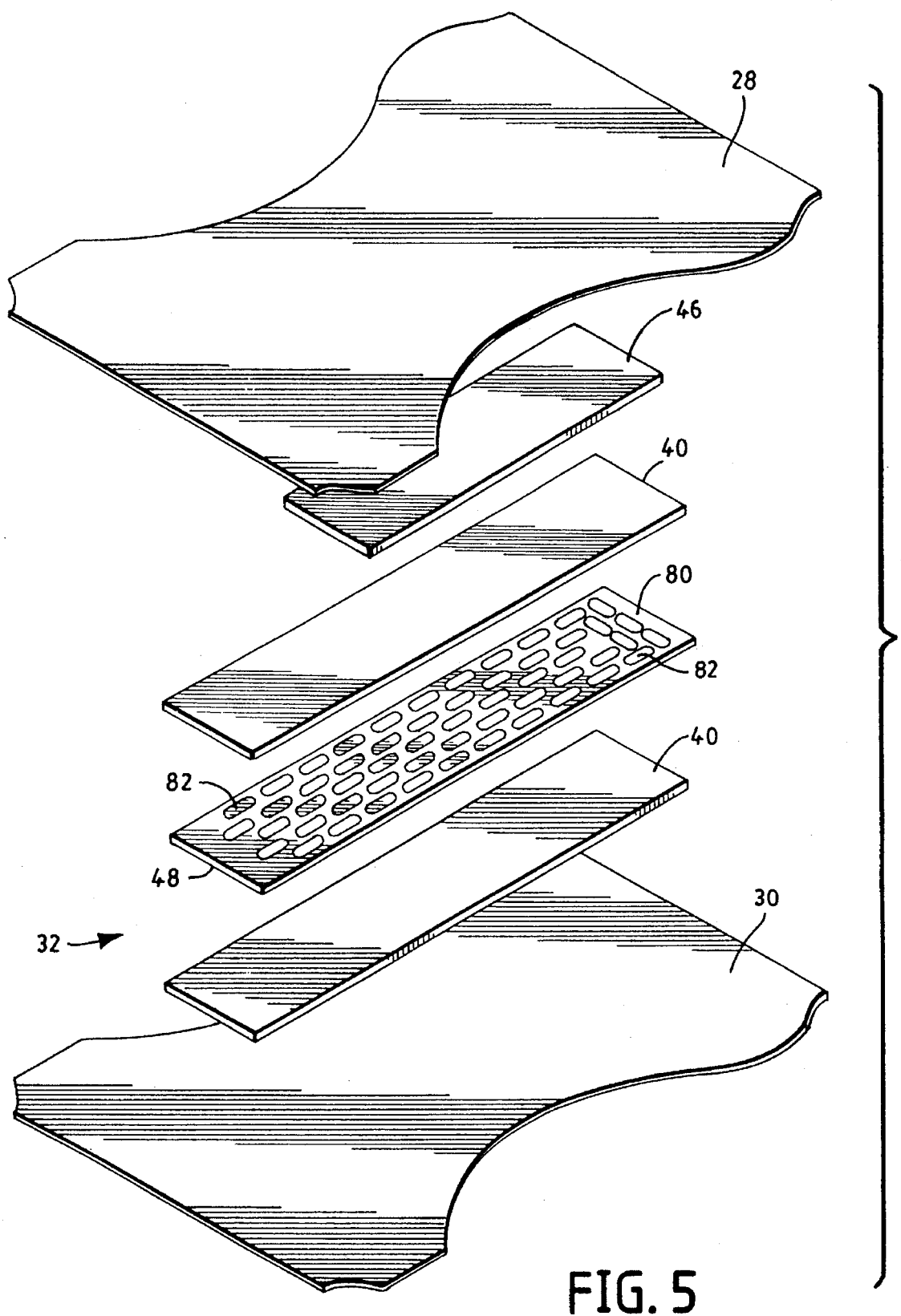
FIG. 5 representatively shows an expanded, perspective view of an article of the invention having a retention portion which includes superabsorbent material held in discrete pocket regions.

With reference to FIG. 5, the retention portion 48 of diaper 10 can include a superabsorbent absorbent laminate 80, and a fibrous web layer 40 can be located on either the outerside or bodyside of the absorbent laminate, or located on both the outerside and bodyside of the absorbent laminate. The absorbent laminate 80 includes particles of high-absorbency material, such as superabsorbent polymer, which are held in a plurality of individual, discrete pocket regions 82. The pocket regions are spaced apart on a major facing surface of at least one liquid permeable web, and in particular arrangements, the pocket regions can be formed and sandwiched between first and second liquid permeable webs 84 and 86, respectively (FIG. 6). In desired arrangements, either or both of the liquid permeable webs can be provided by a fibrous web layer 40. Examples of suitable superabsorbent laminate structures having discrete pocket regions are described in U.S. patent application Ser. No. 145,926 of R. Tanzer et al., which was filed Oct. 29, 1993 and entitled ABSORBENT ARTICLE WHICH INCLUDES SUPERABSORBENT MATERIAL LOCATED IN DISCRETE, ELONGATE POCKETS ARRANGED IN SELECTED PATTERNS (attorney docket No. 10,902).

To provide the desired thinness to the various configurations of the final absorbent article, the retention portion 48 can be configured with an overall bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.4 kPa).

It should be readily appreciated that the density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.4 kPa). Conventional thickness measuring devices may be employed to determine the thickness needed to calculate the density.

In particular aspects of the invention, the absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article can have a cross-directional width of about 9.0 inches (about 22.8 cm), the narrowest portion of the crotch section can have a width of about 3.5 inches (about 8.9 cm) and the back waistband region can have a width of about 4.5 inches (about 11.4 cm).

The following examples are presented to provide a more detailed understanding of the invention. The EXAMPLES are intended to be representative, and are not intended to specifically limit the scope of the invention.

EXAMPLES

Examples 1–9

Sample 1 was a 100% fluff, airlaid web composed of fiberized, bleached kraft wood pulp. The wood pulp was Kimberly-Clark Coosa River CR-2054 fluff pulp, which was a blend of 20% southern hardwood and 80% southern softwood. The base pulp was obtained from Kimberly-Clark Corporation's pulp mill at Coosa Pines, Ala. 35044-0555. The wood pulp was dry fiberized and densified to form the final airlaid web.

Sample 2 was a creped wadding composed of a high-porosity, low basis weight, creped softwood tissue which is available from Kimberly-Clark Corporation under the Kimberly-Clark raw material specification RM-7088, and has typically been referred to as "forming tissue". The creped tissue had a Frazier Porosity of about 300 standard cubic feet per minute per square foot of tested surface area (scf/min/ft$^2$), and had a basis weight of about 17 gsm. The creped wadding also has a maximum resin content of about 0.5% w/w (10 lb dry polymer/ton dry fiber).

Sample 3 was a wet-shaped, through-air dried, premium consumer paper towel manufactured by the Procter and Gamble Company (Cincinnati, Ohio) and sold under the trademark BOUNTY.

Sample 4 was a conventionally wet pressed, economy paper towel made by Kimberly-Clark Corporation and sold under the trademark HI-DRI®.

Sample 5 was a double re-creped, high performance consumer paper towel made by Scott Paper Corp. (Philadelphia, Pa.) and sold under the trademark JOB SQUAD.

Sample 6 was a hydroentangled, nonwoven-reinforced, disposable, manufactured rag produced by Kimberly-Clark Corporation and sold under the trademark WORKHORSE®.

Sample 7 was a co-formed web composed of continuous polypropylene meltblown microfiber (35% by weight) and wood fluff pulp (65% by weight).

Sample 8 was an airformed web composed of a blend of superabsorbent particles (6% by weight) and softwood fluff pulp (92% by weight), which has been reinforced with 2% by weight melt-sprayed polypropylene microfiber. The web structure has been used to construct the absorbent core of the incontinence undergarment produced by Kimberly-Clark Corporation and sold under the trademark DEPEND®.

Sample 9 was an airformed web composed of a blend of superabsorbent particles (40% by weight) and wood fluff pulp (60% by weight). The web has been used to construct the absorbent core of the disposable baby diaper produced by Kimberly-Clark Corporation and sold under the trademarks HUGGIES® UltraTrim.

Figure 7:
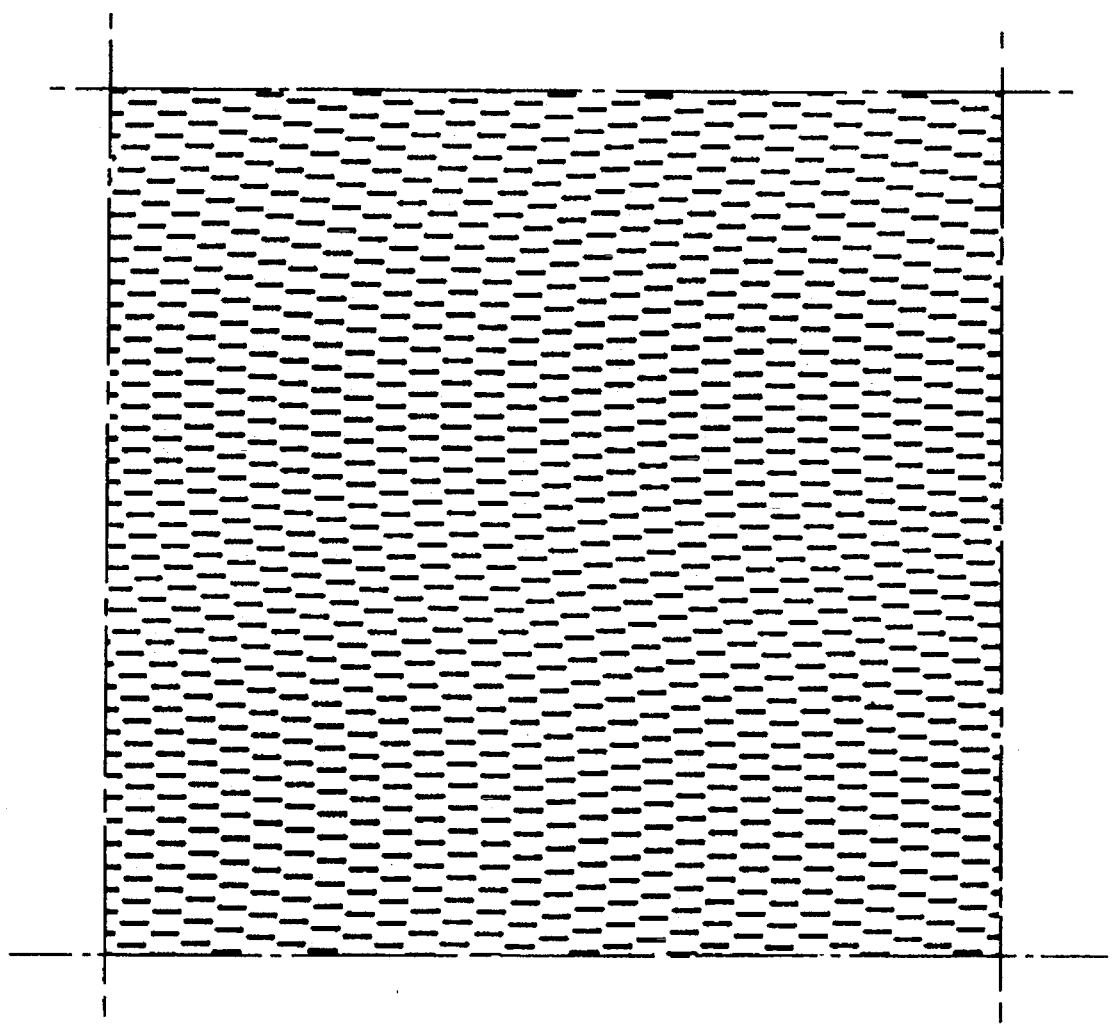
FIG. 7 representatively an embossing pattern configured on the surface of an embossing roll employed to prepare sample pulp sheet materials.

Samples 1–9 had the parameters and properties listed on FIG. 7.

Examples 10–13, 15, 16 and 19

Samples 10–13, 15, 16 and 19 were composed of pulp boards which were produced by a conventional wet-forming, wet pressing method. In particular, the wet-pressed pulp board basesheets were produced on a 24-inch (about 61 cm) pilot fourdrinier paper machine at Western Michigan University, McCracken Hall, Kalamazoo, Mich. 49008-5060. After pressing, the basesheets were conventionally dried on steam-heated dryer cans. Samples 12, 16 and 19 were further processed by micro-straining in accordance with the parameters that are set forth in more detail in Table 1 below.

TABLE 1

| Sample No. | Pattern Engagements (inches) | | | |
|---|---|---|---|---|
| | Pass | 1804 | SZ | SPEED (fpm) |
| 12 | 1 | 0.022 | 0.015 | 100 |
| | 2 | 0.022 | 0.015 | 100 |
| | 3 | 0.022 | 0.015 | 100 |
| | 4 | 0.010 | 0.005 | 100 |
| | 5 | 0.010 | 0.005 | 100 |
| | 6 | 0.010 | 0.005 | 100 |
| 16 | 1 | 0.010 | 0.003 | 100 |
| | 2 | 0.010 | 0.003 | 100 |
| | 3 | 0.010 | 0.003 | 100 |
| | 4 | 0.010 | 0.003 | 100 |
| 19 | 1 | 0.020 | 0.004 | 100 |
| | 2 | 0.020 | 0.004 | 100 |
| | 3 | 0.020 | 0.004 | 100 |
| | 4 | 0.015 | 0.002 | 100 |
| | 5 | 0.015 | 0.002 | 100 |
| | 6 | 0.015 | 0.002 | 100 |

(cm = inches × 2.54)

Examples 14, 17, 18, and 20–23

Samples 14, 17, 18, and 20–23 were produced by a conventional through-air drying technique. In particular, the through-air dried pulpboard basesheets were produced on a 24 inch (about 61 cm) Rotoformer machine at the Herty Foundation's Research and Development Center, P.O. Box 7798, Savannah, Ga. 31418. Drying was conducted without pressing by passing the sheet over a Honeycomb through-air dryer. Samples 20–23 were further processed by micro-straining in accordance with the parameters that are set forth in more detail in Table 2 below.

TABLE 2

| Sample No. | Pattern Engagements (inches) | | | |
|---|---|---|---|---|
| | Pass | 1804 | SZ | SPEED (fpm) |
| 22 | 1 | 0.01 | 0.003 | 100 |
| | 2 | 0.01 | 0.003 | 100 |
| 20 | 1 | 0.018 | 0.01 | 100 |
| | 2 | 0.018 | 0.01 | 60 |
| | 3 | 0.018 | 0.003 | 40 |

TABLE 2-continued

| | Pattern Engagements (inches) | | | |
|---|---|---|---|---|
| Sample No. | Pass | 1804 | SZ | SPEED (fpm) |
| 21 | 1 | 0.018 | 0.010 | 100 |
| | 2 | 0.018 | 0.010 | 100 |
| | 3 | 0.018 | 0.003 | 100 |
| 23 | 1 | 0.015 | 0.003 | 100 |
| | 2 | 0.015 | 0.003 | 80 |
| | 3 | 0.015 | 0.003 | 60 |

(cm = inches × 2.54)

Microstraining Process and Conditions under which Pulp Sheets were Strained

Pulp rolls were microstrained by working the pulp sheet through the nip between pairs of counter-rotating engraved metal rolls which had been gapped to mechanically soften the sheet without cutting or tearing. Multiple passes were often required to produce a desired amount of sheet softening. A typical pass consisted of working the sheet between the elements of the 1804 and SZ patterns. The engagements and speeds for the microstrained pulps used in this investigation are shown in Tables 1 and 2 above.

Both the 1804 and S/Z patterns are provided by a matched pair of steel male and female rolls run in a fixed gap process. With reference to FIG. 7, the pattern 1804 male roll has male elements with a height of 2.54 millimeters, a side wall angle of 30°, a length of 4 millimeters, and a width of 1.0 millimeter, hence having a length-to-width ratio of 4:1. The elements are oriented with the major axis of the elements parallel to the axial direction of the roll. There are an average of 0.13 male elements per millimeter in the axial direction of the roll and an average of 0.5 male elements per millimeter in the circumferential direction of the roll, resulting in an element density of 6.2 elements per square centimeter. The male elements are arranged in a sinusoidal pattern resulting in a pattern repeat of 94 millimeters. The female roll has cooperating voids with corresponding dimensions and orientations.

Figure 8:
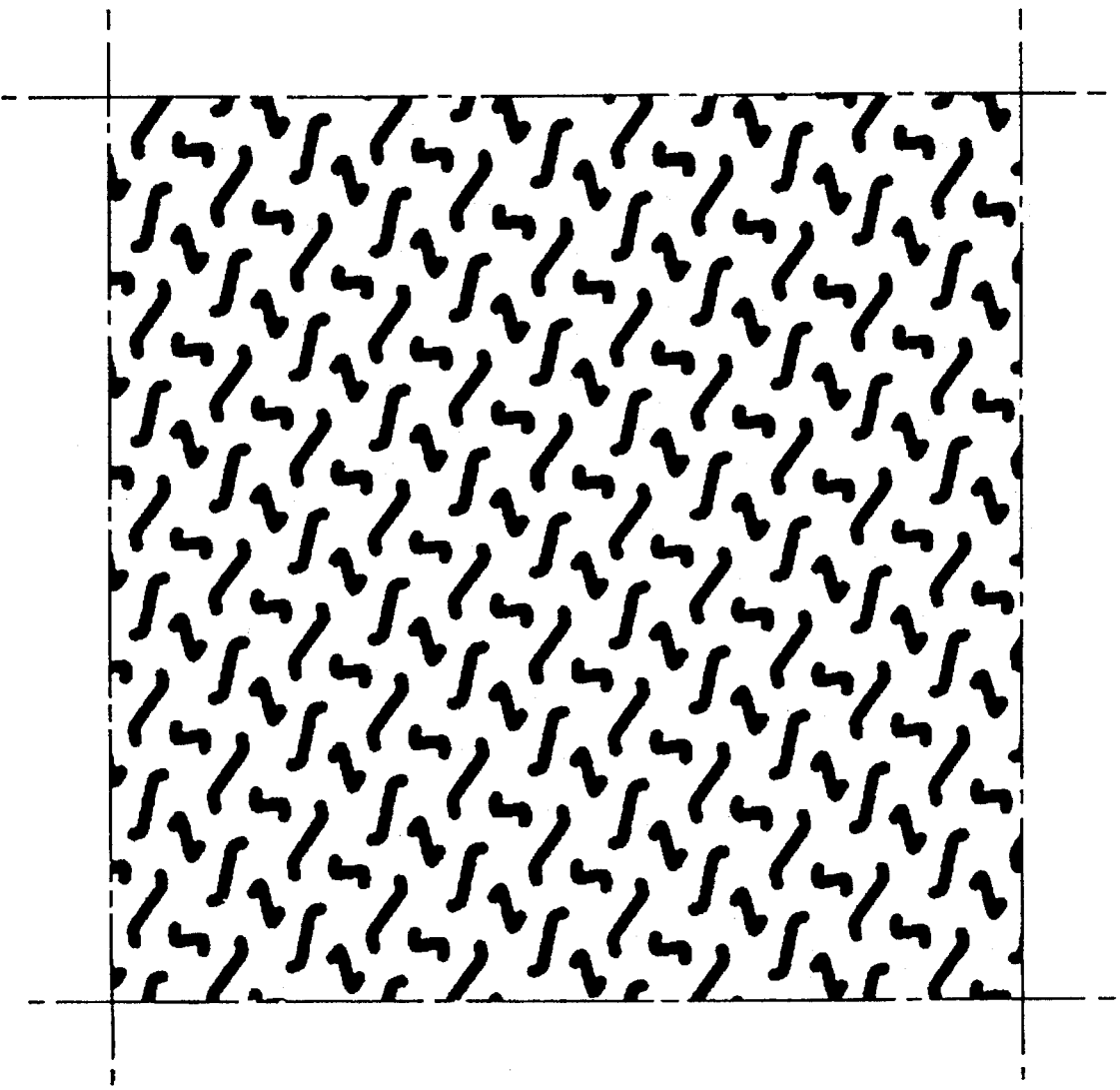
FIG. 8 representatively shows another embossing pattern configured on the surface of an embossing roll employed to prepare other sample pulp sheet materials.

With reference to FIG. 8, the S/Z wormy pattern male element has a height of 8.6 millimeters, a side wall angle of 33°, an element surface area of 0.035 square centimeters, an element density of 8.5 elements per square centimeter, an embossing area of about 30%, and a pattern repeat length of 7.6 millimeters. The male elements are made up of two distinct design elements. The female roll has cooperating voids of with corresponding dimensions and orientations.

Test Procedures The following test procedures were employed to assess the Samples.

45-Degree Liquid Intake

2"×10" (about 5.1 cm×25 cm) samples of absorbent material were cut and placed on a plexiglass board having an incline of 45 degrees. Fifty (50) milliliters of 0.9% saline solution (e.g. Baxter Scientific, Catalog Number B3158-3) were weighed and placed in a funnel positioned above the sample at a location 2 inches (about 5.1 cm) from the uppermost end of the absorbent. The stopcock was opened to allow the entire 50 ml dose to contact the sample. The initial (dry) and final (wet) weights of the samples were obtained and the quantity of fluid retained in the sample was determined by difference.

Tensile Testing

Tensile testing was conducted on a tensile test apparatus, such as an Instron Model No. 4201. The test samples were cut to 1" (2.54 cm) width, the jawspan was 3" (7.6 cm), and the crosshead speed was 0.5 in/min (1.27 cm/min).

Blotter Test

The ability of samples to absorb liquid and hold it under load was determined by soaking the samples in excess saline, and then blotting liquid from the samples with absorbent paper under an imposed load according to the following procedure.

A dry 3"×7" (about 7.6 cm×17.8 cm) sample was weighed, placed on a coarse screen for physical support, and soaked in excess 0.9% saline for 2 minutes. After soaking, the sample was removed from the saline solution and allowed to drain against a 5-degree board until liquid no longer drained from the sample (60–180 seconds). The drained sample was then weighed. Each sample was then placed between a pair of 4"×8" (about 10.1 cm×20.3 cm) sheets of James River Verigood (No. 411-01-13) absorbent blotter paper under a weight to impose a pressure of 0.35 psi (about 2.4 kPa). Three pairs of blotter sheets were used in succession at time intervals of 60–90 seconds. Following the blotting, the sample was again weighed.

The amount of liquid saline expressed from the sample is the difference between the wet sample (W) weight and the blotted sample (B) weight. This difference is divided by the initial dry sample weight (D) to report the amount of expressed liquid on a "grams of liquid per gram of sample" basis.

$$\text{grams of liquid per gram of sample} = (W-B)/D$$

Caliper Testing

The calipers (thicknesses) of the Samples were obtained using the following device:

Digimatic Thickness Tester

Model Number 543-445-1

Type ID-1050ME

Mitutoyo Mfg. Co. Ltd.

This tester has a range of 0.001"–2" (0.00254 cm–5.1 cm) and a resolution of 0.01 mm.

After zeroing the instrument, the weighted foot was gently placed on the sample and the thickness recorded from the digital readout. Three measurements were recorded per sample. The circular foot on the Digimatic tester had a mass of 633 grams and a diameter of 76 mm, providing a pressure of approximately 0.2 psi (1.4 kPa).

Characteristics and Parameters of the Samples

The compositional and physical characteristics of the Samples were determined and are summarized in the tables of FIGS. 9 and 10. With reference to FIGS. 9 and 10, it can be seen that the softened sheets of the invention can maintain high levels of absorbency in combination with low stiffnesses and relatively high tensile strengths.

The tensile strengths were measured with the above-described tensile testing procedure using a 100 pound load cell, and the geometric mean, peak tensile strength values were determined for the various samples in the following manner:

Let $C_i$; $C_1, C_2, \ldots C_n$; represent the experimental cross-machine direction (c.d.) peak tensile strength values for a given sample, where the c.d. extends along the general plane of the sample.

Let $M_j$; $M_1, M_2, \ldots M_p$; represent the experimental machine direction (m.d.) peak tensile strength values for a given sample, where the machine direction extends along the general plane of the sample and is perpendicular to the cross-machine direction.

Calculate the average geometric mean tensile strength, G, from all permutations of the cross-machine direction and machine direction tensile strengths:

$G$ = average of $G_{ij}$
=> average of; $G_{11}, G_{12}, G_{21}, G_{22}, \ldots G_{np}$
=> average of; $(C_1 * M_1)^{1/2}, (C_1 * M_2)^{1/2},$
$(C_2 * M_1)^{1/2}, (C_2 * M_2)^{1/2}, \ldots (C_n * M_p)^{1/2}$ The quantities "n" and "p" are at least 3, and typically are equal and within the range of 3–5.

The calculation of the average geometric mean tensile strength can be represented by the following formula:

$$G = \frac{1}{n*p} * \left[ \sum_{i=1}^{n} \sum_{j=1}^{p} (C_i * M_j)^{1/2} \right]$$

The geometric mean, peak tensile strength data for the indicated Sample numbers are summarized in the table shown in FIG. 11. For each of the Samples, the table lists the minimum (min) and maximum (max) values, along with the arithmetic mean (average) of the measured values. The values are expressed in terms of grams-force per centimeter of sample width, and the identification Sample numbers correspond to the Samples presented in FIG. 9.

Figure 12:
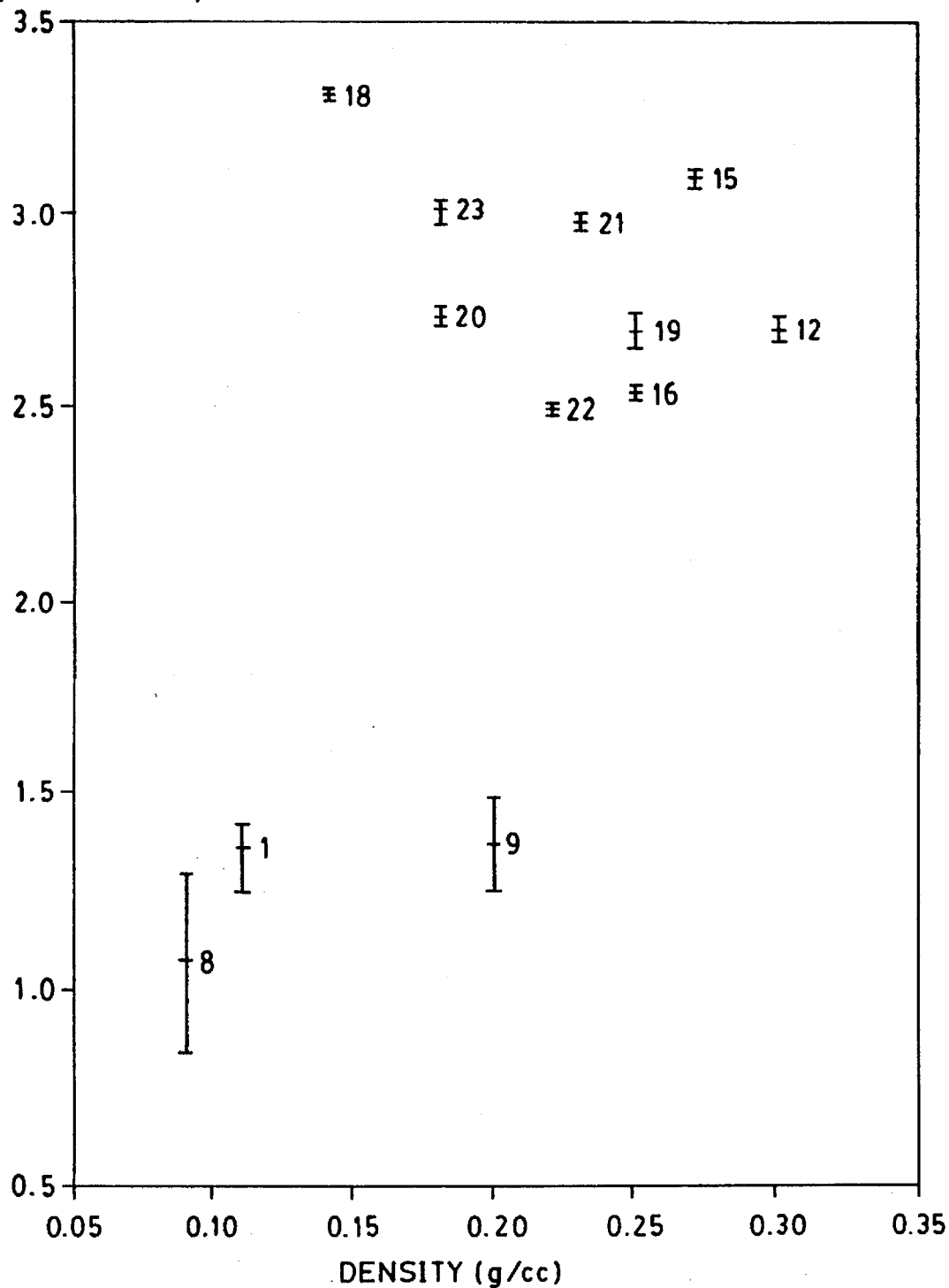
FIG. 12 is a graph which shows a representative plot of the logarithm of particular peak geometric mean tensile force values as a function of density for particular sample materials.

FIG. 12 shows representative plots of the logarithm (base 10) of the geometric mean, peak tensile strength values as a function of density for particular sample materials, and the identification Sample numbers correspond to the Samples presented in FIG. 11. The middle cross bar for each identified Sample represents the logarithm ($\log_{10}$) of the arithmetic average of the geometric mean peak tensile strength values that were determined for the identified Sample. The high and low cross bars represent the logarithms of the maximum and minimum values, respectively, of the geometric mean peak tensile strengths that were determined for the Sample.

With reference to FIGS. 11 and 12, it can be seen that samples of materials having various configurations of the present invention, such as samples 19, 20, 21, 22 and 23, exhibited an advantageous combination of strength and density. For example, samples 19–23 had much greater tensile strengths than some ordinary absorbent materials, such as samples 1, 8 and 9, without the high density of samples 12 and 15. More particularly, representative samples of the materials of the present invention provided a high strength even though the densities of the materials were less than about 0.25 gm/cc. The combination of relatively high strength and low density in a predominately cellulosic web can make the materials of the present invention particularly desirable for absorbent products.

Having described the invention in rather full detail, it will be readily apparent that various changes and modifications can be made without departing from the spirit of the invention. All of such changes and modifications are contemplated as being within the scope of the invention, as called for by the subjoined claims.

We claim:

1. An article, comprising:
at least one absorbent fibrous web layer which is substantially non-hydroentangled, said fibrous web layer having a basis weight of at least about 60 gsm, a density of not more than about 0.25 gm/cc, a peak geometric mean tensile strength of at least about 250 grams-force per centimeter of width of said fibrous web layer, a Gudey stiffness to thickness quotient of not more than about 4000 SGU/mm, and having a fiber content in which at least about 90 wt % of said fiber content are fibers having a fiber length of not more than about 0.4 inch (about 1 cm).

2. An article, comprising:

a backsheet layer;

a liquid permeable topsheet layer which is disposed in facing relation with said backsheet layer; and an absorbent structure which is interposed between said backsheet layer and topsheet layer and has an overall absorbent capacity of at least about 300 gm of saline, said absorbent structure including at least one absorbent fibrous web layer which is substantially non-hydroentangled, said fibrous web layer having a basis weight of at least about 60 gsm, a density of not more than about 0.25 gm/cc, a peak geometric mean tensile strength of at least about 250 grams-force per centimeter of width of said fibrous web layer, and having a fiber content in which at least about 90 wt % of said fiber content are fibers having a fiber length of not more than about 0.4 inch.

3. An article as recited in claim 1 or 2, wherein said article includes a plurality of said fibrous web layers.

4. An article as recited in claim 1 or 2, wherein said article includes a retention portion having particles of superabsorbent material held in a plurality of discrete pocket regions of said retention portion.

5. An article as recited in claim 1 or 2, wherein said article includes a retention portion having particles of superabsorbent material held in a plurality of individual, discrete pocket regions which are provided for by said at least one fibrous web layer.

6. An article which comprises particles of superabsorbent material held in a plurality of individual pocket regions, said pocket regions sandwiched between first and second liquid permeable, non-hydroentangled fibrous web layers, each of said first and second web layers having a basis weight of at least about 60 gsm, a density of not more than about 0.25 gm/cc, a peak geometric mean tensile strength of at least about 250 grams-force per centimeter of width of said fibrous web layer, and each having a fiber content in which at least about 90 wt % of said fiber content are fibers having a fiber length of not more than about 0.4 inch (about 1 cm).

7. An article as recited in claim 6, wherein said first and second web layers are interconnected to define said pocket regions.

8. An article as recited in claim 1, 2 or 6, wherein at least about 95 wt % of said fiber content are fibers having a fiber length of not more than about 0.4 inch (about 1 cm).

9. An article as recited in claim 1, 2 or 6, wherein at least about 98 wt % of said fiber content are fibers having a fiber length of not more than about 0.4 inch (about 1 cm).

10. An article as recited in claim 1, 2 or 6, wherein not more than about 5 wt % of said fiber content of each fibrous web layer are fibers having a fiber length of at least about 1.2 inch (about 3 cm).

11. An article as recited in claim 2 or 6, wherein said fibrous web layer further includes a Gurley stiffness to thickness quotient of not more than about 4000 SGU/mm.

12. An article as recited in claim 1, 2 or 6, wherein each said fibrous web layer further includes a Gurley stiffness to thickness quotient of not more than about 2000 SGU/mm.

13. An article as recited in claim 1, 2 or 6, wherein each said fibrous web layer further includes a Gurley stiffness to thickness quotient of not more than about 1000 SGU/mm.

14. An article as recited in claim 1, 2 or 6, wherein each said fibrous web layer is substantially free of binder material.

15. An article as recited in claim 1, 2 or 6, wherein each said fibrous web layer includes not more than about 1.5 wt % of binder material.

16. An article as recited in claim 1, 2 or 6, wherein each said fibrous web layer includes not more than about 5 wt % of binder material.

17. An article as recited in claim 1, 2 or 6, wherein each said fibrous web layer has a basis weight of at least about 100 gsm.

18. An article as recited in claim 1, 2 or 6, wherein each said fibrous web layer has a basis weight of at least about 125 gsm.

19. An article as recited in claim 1, 2 or 6, wherein said article includes a retention portion having a mixture of woodpulp fluff and particles of superabsorbent material.

20. An article as recited in claim 1, 2 or 6, wherein said fiber content of each said web layer is at least about 95 wt % cellulosic fibers.

21. An article as recited in claim 1, 2 or 6, wherein said fiber content of each said web layer is substantially 100 wt % cellulosic fibers.

22. An article as recited in claim 1, 2 or 6 wherein said fibrous web layer has a thickness of not more than about 4 mm.

* * * * *